US 007740063B2

(12) United States Patent
Fallon et al.

(10) Patent No.: US 7,740,063 B2
(45) Date of Patent: Jun. 22, 2010

(54) METHOD FOR IDENTIFICATION OF NOVEL ANAEROBIC DENITRIFYING BACTERIA UTILIZING PETROLEUM COMPONENTS AS SOLE CARBON SOURCE

(75) Inventors: Robert D. Fallon, Elkton, MD (US);
Linda L. Hnatow, Oxford, PA (US);
Scott Christopher Jackson, Wilmington, DE (US); Sharon Jo Keeler, Bear, DE (US)

(73) Assignee: E.I. du Pont de Nemours and Company, Wilmington, DE (US)

( * ) Notice: Subject to any disclaimer, the term of this patent is extended or adjusted under 35 U.S.C. 154(b) by 0 days.

(21) Appl. No.: 12/194,794

(22) Filed: Aug. 20, 2008

(65) Prior Publication Data
US 2010/0044031 A1 Feb. 25, 2010

(51) Int. Cl.
*E21B 43/22* (2006.01)
(52) U.S. Cl. .................. 166/246; 166/250.01; 166/264
(58) Field of Classification Search ........................ None
See application file for complete search history.

(56) References Cited

U.S. PATENT DOCUMENTS 5,492,828 A 2/1996 Premuzic et al.

FOREIGN PATENT DOCUMENTS

WO 01/33040 5/2001
WO 2006/108138 A2 10/2006

OTHER PUBLICATIONS

Almeida et al., Engineering in Life Sciences, vol. 4, No. 4, pp. 319-325, 2004.
Rueter et al., Nature, vol. 372, No. 6505, pp. 455-458, 1994.
Partidas et al., Oil and Gas Journal, vol. 96, No. 24, pp. 62-64, 1998.
International Search Report of related PCT/US2008/073954 mailed Nov. 14, 2008.
U.S. Appl. No. 10/564,365, filed Jun. 2, 2006, Lal Banwari.
A. M. Lesk, Computational Molecular Biology, 1988, Oxford University Press, NY (Book Not Included).
D. W. Smith, Biocomputing: Informatics and Genome Projects, 1993, Academic Press, NY (Book Not Included).
A. M. Griffin, Computer Analysis of Sequences Data, Part 1, 1994, Humana Press, NJ (Book Not Included).
G. Heinje, Sequence Analysis in Molecular Biology, 1987, Academic Press (Book Not Included).
M. Gribskov et al., Sequence Analysis Primer, 1991, Stockton Press, NY (Book Not Included).
Altschul et al., Basic Local Alignment Search Tool, J. Mol. Biol., 1990, vol. 215:403-410 (Book Not Included).
W. R. Pearson, Searching Protein Sequence Databases—Is Optimal Best, Comput. Methods Genome Res., 1992, pp. 111-120.
A. Loy et al., Microarray and Functional Gene Analyses of Sulfate-Reducing Prokaryotes in Low-Sulfate, Acidic Fens Reveal Cooccurrence of Recognized Genera and Novel Lineages, Appl. Environ. Microbiol., 2004, vol. 70:6998-7000.

A. Loy et al., Oligonucleotide Microarray for 16S rRNA Gene-Based Detection of All Recognized Lineages of Sulfate-Reducing Prokaryotes in the Environment, Appl. Environ. Microbiol., 2002, vol. 68:5064-5081.
J. Liebich et al., Improvement of Oligonucleotide Probe Design Criteria for Functional Gene Microarrays in Environmental Applications, Appl. Environ. Microbiol., 2006, vol. 72:1688-1691.
A. Grabowski et al., Microbial Diversity in Production Waters of a Low-Temperature Biodegraded Oil Reservoir, FEMS Micro ECO, 2005, vol. 544:427-443.
G. C. Baker et al., Review and Re-Analysis of Domain-Specific 16S Primers, J. Microbiol. Meth., 2003, vol. 55:541-555.
W. Ludwig et al., ARB: A Software Environment for Sequence Data, Nucleic Acids Res., 2004, vol. 32:1363-1371.
Watanabe et al., Population Dynamics of Phenol-Degrading Bacteria in Activated Sludge Determinded by GYRB-Targeted Quantitative PCR, Appl. Environ. Microbiol., 1998, vol. 64:1203-1209.
M. E. Davey, Isolation of Three Species of Geotoga and Petrotoga: Two New Genera, Representing a New Lineage in the Bacterial Line of Descent Distantly Related to the Thermotogales, Syst. Appl. Microbiol., 1993, vol. 16:191-200.
T. Lien et al., *Petrotoga mobilis* Sp. Nov., from a Noeth Sea Oil-Production Well, Int. J. Syst. Bacteriol., 1998, vol. 48:1007-1013.
S. Breinig et al., Genes Involved in Anaerobic Metabolism of Phenol in the Bacterium Thauera Aromatica, J. Bacteriol., 2000, vol. 182:5849-5863.
B. Leuthner et al., Anaerobic Toluene Catabolism of Thauera Aromatica: The BBS Operon Codes for Enzymes of B Oxidation of the Intermediate Benzylsuccinate, J. Bacteriol., 2000, vol. 182:272-277.
B. Song et al., Characterization of Halobenzoate-Degrading Denitrifying Azoarcus and Thauera Isolates and Description of *Thauera chlorobenzoica* Sp. Nov., Int. J. Syst. Evol. Microbiol., 2001, vol. 51:589-602.
K. H. Nealson et al., Iron and Manganese in Anaerobic Respiration: Environmental Significance, Physiology, and Regulation, Ann. Rev. Microbiol., 1994, vol. 48:311-343.
K. H. Nealson et al., Anaerobic Electron Acceptor Chemotaxis in *Shewanella putrefaciens*, Appl. Eniron. Microbioil., 1995, vol. 61:1551-1554.
G. M. Bertoni et al., Analysis of the Gene Cluster Encoding Toluene/o-Xylene Monooxygenase From Pseudomonas Stutzeri OX1, Appl. Envrion. Microbiol., 1998, vol. 64:3626-3632.
K. J. Rockne, Anaerobic Naphthalene Degradation by Microbial Pure Cultures Under Nitrate-Reducing Conditions, Appl. Environ. Microbiol., 2000, vol. 66:1595-1601.
D. P. Labeda, Isolation of Anaerobic Microorganisms, Isolation of Biotechnological Organisms From Nature, 1990, pp. 117-140.
C. Moreno-Vivian et al., Prokaryotic Nitrate Reduction: Molecular Properties and Functional Distinction Among Bacterial Nitrate Reductases, J. Bacteriol., 1999, vol. 181:6573-6584.
M. M. Deangelis et al., Solid-Phase Reversible Immobilization for the Isolation of PCR Products, Nucleic Acid Res., 1995, vol. 23:4742-4743.
Ewing et al., Base-Calling of Automated Sequencer Traces Using Phred. I. Accuracy Assessment, Genome Res., 1985, vol. 8:175-185.
J. R. Cole et al., The Ribosomal Database Project (RDP-II): Sequence and Tools for High-Throughput rRNA Analysis, Nucleic Acid Res., 2005, vol. 33:294-296.

*Primary Examiner*—Zakiya W. Bates (57) ABSTRACT

A method for the phylogenetic identification of indigenous anaerobic denitrifying bacterial species in an oil well is described. The method avoids the process of enrichment of microbial samples.

13 Claims, 1 Drawing Sheet

Figure 1

METHOD FOR IDENTIFICATION OF NOVEL ANAEROBIC DENITRIFYING BACTERIA UTILIZING PETROLEUM COMPONENTS AS SOLE CARBON SOURCE

FIELD OF INVENTION

This invention relates to the field of environmental microbiology and modification of heavy crude oil properties using microorganisms. More specifically, pure anaerobic denitrifying microorganisms are identified and applied to modify the properties of heavy crude oil.

BACKGROUND OF THE INVENTION

The challenge to meet the ever increasing demand for oil includes increasing crude oil recovery from heavy oil reservoirs. This challenge has resulted in expanding efforts to develop alternative cost efficient oil recovery processes (Kianipey, S. A. and Donaldson, E. C. 61$^{st}$ Annual Technical Conference and Exhibition, New Orleans, La., USA, Oct. 5-8, 1986). Heavy hydrocarbons in the form of petroleum deposits and oil reservoirs are distributed worldwide. These oil reserves are measured in the hundreds of billions of recoverable barrels. Because heavy crude oil has a relatively high viscosity, it is essentially immobile and cannot be easily recovered by conventional primary and secondary means.

Microbial Enhanced Oil Recovery (MEOR) is a methodology for increasing oil recovery by the action of microorganisms (Brown, L. R., Vadie, A. A,. Stephen, O. J. SPE 59306, SPE/DOE Improved Oil Recovery Symposium, Oklahoma, 3-5—Apr., 2000). MEOR research and development is an ongoing effort directed to developing techniques to use microorganisms to modify crude oil properties to benefit oil recovery (Sunde. E., Beeder, J., Nilsen, R. K. Torsvik, T., SPE 24204, SPE/DOE 8$^{th}$ Symposium on enhanced Oil Recovery, Tulsa, Okla., USA, Apr. 22-24, 1992).

Methods for identifying microorganisms useful in MEOR processes have been described. These methods require identification of samples drawn from an oil well or reservoir comprising a consortium of microorganisms and enrichment or evolution of populations in the sample, under specific conditions with defined nutrient media. See, U.S. patent application Ser. No. 10/564,365.

Microbial degradation of hydrocarbons has also been described, under aerobic or mixed (aerobe and anaerobic) conditions, as a mechanism for oil viscosity reduction. Degradation under these circumstances requires evolved microorganisms and particular nutrients which have not been demonstrated as an economic means for improving oil recovery (See, U.S. Pat. No. 5,492,828).

Thus, there is a need for developing methods to: 1) identify microorganisms that could be used to enhance oil recovery under economic conditions; 2) identify microorganisms that can grow on oil under anaerobic conditions without the need for nutrient supplementation or long term enrichment of indigenous microorganisms; and 3) use said identified microorganisms, in a cost-efficient way, to improve oil recovery.

SUMMARY OF THE INVENTION

The methods described herein meet the needs identified above, by describing methods of identifying indigenous bacterial genera, and using phylogenetic identification techniques based on the phylogeny of the indigenous genera to select pure anaerobic bacterial cultures that respire by denitrification and that are capable of growing on oil without complex nutrient supplementation.

Further, the methods are described for using said pure cultures, without enrichment or directed evolution, to economically enhance oil recovery. These pure cultures are used to enhance oil recovery in one or more of the following ways: (1) alter the permeability of the subterranean formation to improve water sweep efficiency; (2) produce biosurfactants which decrease surface and interfacial tensions; (3) mediate changes in wettability; (4) produce polymers which facilitate mobility of petroleum; and (5) generate gases (predominantly $CO_2$) that increase formation pressure and reduce oil viscosity.

Specifically, this invention relates to the application of rDNA phylogenetic typing of bacteria found in environmental samples obtained from an oil well or reservoir, followed by identifying and obtaining pure cultures of known bacterial species with similar genetic make up, then screening these strains for relevant functionalities, such as capability to grow on crude oil under denitrifying conditions.

In one embodiment this invention describes a method for improving oil recovery from an oil well comprising:
a) providing an environmental sample comprising indigenous microbial populations from said environmental sample;
b) identifying the microbial genera present in said environmental sample by phylogenetic typing;
c) selecting from one or more known pure culture species from the genera identified in (b), wherein said species are capable of growing on oil; and
d) identifying relevant functionalities of the species of (c) for use in improving oil recovery.

In one aspect, the invention provides that improved oil recovery occurs by reduction in crude oil viscosity by growth of a species in (c) having certain functionalities identified by step (d) in a oil reservoir, wherein said growth results in the production of any one of biosurfactants, carbon dioxide, or cell mass, and selective degradation of high molecular weight components in the oil well or combinations thereof.

In another embodiment, improving oil recovery is improved by growth of a species of (c) having certain functionalities identified by step (d) in an oil well under anaerobic and denitrifying conditions substantially without corrosion of recovery and processing hardware.

In another embodiment phylogenetic mapping is used to predict the nutrients needed to selectively encourage growth of particular species over others.

BRIEF DESCRIPTION OF FIGURES AND SEQUENCES OF THE INVENTION

The invention can be more fully understood from the following detailed description, FIG. 1, and the accompanying sequence descriptions, which form a part of this application.

The following sequences conform with 37 C.F.R. 1.821-1.825 ("Requirements for Patent Applications Containing Nucleotide Sequences and/or Amino Acid Sequence Disclosures—the Sequence Rules") and are consistent with World Intellectual Property Organization (WIPO) Standard ST.25 (1998) and the sequence listing requirements of the EPO and PCT (Rules 5.2 and 49.5(a-bis), and Section 208 and Annex C of the Administrative Instructions. The symbols and format used for nucleotide and amino acid sequence data comply with the rules set forth in 37 C.F.R. §1.822.

```
                                              SEQ ID NO: 1
8F Forward AGAGTTTGATYMTGGCTCAG-3'

SEQ ID NO: 2
1407R reverse primer 1407R - GACGGGGGTGWGTRCAA-3'
```

SEQ ID NO:1 and SEQ ID NO:2 were used for amplification of the bacterial rDNA genes.

DETAILED DESCRIPTION OF THE INVENTION

The present invention relates to methods of identifying microorganisms useful for improving oil recovery. Specifically the methods described herein are directed to generating a phylogentic map of microorganisms from an oil well and using said phylogenetic map to identify related pure cultures useful in improving oil recovery i.e., cultures that respire by denitrification and are capable of growing on oil without complex nutrient supplementation.

Further, the methods are described for using said identified pure cultures, without enrichment or directed evolution, to economically enhance oil recovery.

The pure cultures identified by the claimed methodologies are used to enhance oil recovery in one or more of the following ways: 1) to alter the permeability of the subterranean formation to improve water sweep efficiency; (2) to produce biosurfactants which decrease surface and interfacial tensions; (3) to mediate changes in wettability; (4) to produce polymers which facilitate mobility of petroleum; and (5) to generate gases (predominantly $CO_2$) that increase formation pressure and reduce oil viscosity; all of which benefit recovery and/or processing of heavy crude oil.

The following definitions are provided for the special terms and abbreviations used in this application:

The abbreviation "PCR" refers to Polymerase chain reaction.

The abbreviation "SDS" refers to Sodium dodecyl sulfate.

The abbreviation "dNTPs" refers to Deoxyribonucleotide triphosphates.

The abbreviation "ATCC" refers to American Type Culture Collection International Depository, Manassas, Va., USA. The abbreviation "ATCC No." refers to the accession number to cultures on deposit with ATCC.

The term "Sarkosyl" is the anionic detergent, N-methylaminoacetic acid.

The abbreviation "ASTM" refers to the American Society for Testing and Materials.

The term "environmental sample" means any sample exposed to hydrocarbons, including a mixture of water and oil. As used herein environmental samples include water and oil samples that comprise indigenous microorganisms useful for phylogetic mapping of genera present in a given sampling area.

The terms "oil well" and "oil reservoir" may be used herein interchangeably and refer to a subterranean or sea-bed formation from which oil may be recovered.

The term "microbial consortium" means a mixture of microorganisms of different species present as a community that provide a synergistic effect for enhancing oil recovery.

The term "microbial populations" means one or more populations of microorganisms present either in samples obtained from oil wells or in an inoculum for injection into an oil well.

The term "growing on oil" means the microbial species are capable of metabolizing hydrocarbons or other organic components of crude petroleum as a nutrient to support growth.

The terms "denitrifying" and "denitrification" mean reducing nitrate for use in respiratory energy generation.

The term "sweep efficiency" means the ability of injected water to 'push' oil through a geological formation toward a producer well The term "pure culture" means a culture derived from a single cell isolate of a microbial species. The pure cultures specifically referred to herein include those that are publicly available in a depository. Additional pure cultures are identifiable by the methods described herein.

The term "relevant functionalities" means the ability to reduce nitrites or nitrates and grow under anaerobic conditions; the ability to use at least one component available in the oil well as a carbon source; the ability to use at least one component in the injected or produced water; the capability of achieving a desired growth rate in the presence of oil; and the ability to grow optimally in an oil well environment; and combinations thereof.

The term "biofilm" means a film or "biomass layer" of microorganisms. Biofilms are often embedded in extracellular polymers, which adhere to surfaces submerged in, or subjected to, aquatic environments.

The term "simple nitrates" and "simple nitrites" refer to nitrite ($NO_2$) and nitrate ($NO_3$).

The term "oxidative corrosion" refers to chemical conversion of a metal to an inferior product which occurs in the presence of air (e.g., oxygen).

The term "piezophilic microorganisms" means microbes that grow optimally at high pressure, e.g., microbes that cannot grow at less than 50 MPa (500 fold atmospheric pressure) pressure, and grow optimally at 80 MPa (800 fold atmospheric pressure).

The term "acidophilic microorganisms" means microbes that grow optimally under acidic conditions—having an optimum growth pH below 6.0 and sometimes as low as pH 1.0.

The term "alkaliphilic microorganisms" means microbes that grow optimally under alkaline conditions—typically exhibiting one or more growth optima within the pH range 8-11 and which typically grows slowly or not at all at or below pH 7.0.

The term "halophilic microorganisms" means microbes that grow optimally in the presence of electrolyte (commonly NaCl) at concentrations above 0.2 M and which typically grows poorly or not at all in low concentrations of electrolyte.

The term "psychrophilic microorganisms" means microorganisms which grow optimally at a temperature of 20° C. or below.

The term "modifying the environment of oil well" includes 1) alter the permeability of the subterranean formation (sweep efficiency), (2) produce biosurfactants which decrease surface and interfacial tensions, (3) mediate changes in wettability, (4) produce polymers which facilitate mobility of petroleum; and (5) generate gases (predominantly $CO_2$) that increase formation pressure; and (6) reduce oil viscosity.

The term "inoculating an oil well" means injecting one or more microorganism populations into an oil well or oil reservoir such that microorganisms are delivered to the well or reservoir without loss of total viability.

The term "phylogenetic typing" "phylogenetic mapping" or "phylogenetic classification" may be used interchangeably herein and refer to a form of classification in which microorganisms are grouped according to their ancestral lineage. The methods herein are specifically directed to phylogenetic typing on environmental samples based on 16S Ribosomal DNA (rDNA) sequencing. In this context, a full 1400 base pair (bp) length of the 16S rDNA gene sequence is generated using primers identified herein and compared by sequence homology to a database of known rDNA sequences of known microorganisms. This comparison is then used for identification of pure cultures for use in enhanced oil recovery.

The term "additional carbon sources", or "complex carbon nutrients" may be used interchangeably herein and refer to the addition of carbon sources in the circumstance where a microorganisms is incapable of growing on oil without additional carbon added.

The term "nutrient supplementation" refers to the addition of nutrients that benefit growth of microorganisms that are capable of using oil as their main carbon source but grow optimally with other additives, such as carbon sources (other than hydrocarbons) such as yeast extract, peptone, succinate, lactate, formate, acetate, propionate, glutamate, glycine, lysine, citrate, glucose, and vitamin solutions.

The term "microbial species" means distinct microorganisms identified based on their physiology, morphology and phylogenetic characteristics using 16S rDNA sequences.

The abbreviation "NCBI" refers to the National Center for Biotechnology Information.

The abbreviation "rDNA" refers to Ribosomal Deoxyribonucleic Acid.

The abbreviation "cDNA" refers to a double-stranded DNA that is complementary to, and derived from, messenger RNA.

The term "archaeal" means belonging to the Archaea—Archaea are a kingdom of microbial species separate from other prokaryotes based on their physiology, morphology and 16S rDNA sequence homologies.

The term "phylogenetics" refers to the study of evolutionary relatedness among various groups of organisms (e.g., species, populations).

The term "rDNA typing" means the process of utilizing the sequence of the gene coding for 16S rDNA to obtain the "closest relative" microbial species by homology to rDNA sequences maintained in several international databases.

The term "complementary" is used to describe the relationship between nucleotide bases that are capable of hybridizing to one another. For example, with respect to DNA, adenosine is complementary to thymine and cytosine is complementary to guanine.

The term "percent identity", as known in the art, is a relationship between two or more polypeptide sequences or two or more polynucleotide sequences, as determined by comparing the sequences. In the art, "identity" also means the degree of sequence relatedness between polynucleotide sequences, as determined by the match between strings of such sequences. "Identity" and "similarity" can be readily calculated by known methods, including but not limited to those described in "Computational Molecular Biology, Lesk, A. M., ed. Oxford University Press, NY, 1988"; and "Biocomputing: Informatics and Genome Projects, Smith, D. W., ed., Academic Press, NY, 1993"; and "Computer Analysis of Sequence Data, Part I, Griffin, A. M., and Griffin, H. G., eds., Humana Press, NJ, 1994"; and "Sequence Analysis in Molecular Biology, von Heinje, G., ed., Academic Press, 1987"; and "Sequence Analysis Primer, Gribskov, M. and Devereux, J., eds., Stockton Press, NY, 1991". Preferred methods to determine identity are designed to give the best match between the sequences tested. Methods to determine identity and similarity are codified in publicly available computer programs.

The term "sequence analysis software" refers to any computer algorithm or software program that is useful for the analysis of nucleotide or amino acid sequences. "Sequence analysis software" may be commercially available or independently developed. Typical sequence analysis software will include, but is not limited to: the GCG suite of programs (Wisconsin Package Version 9.0, Genetics Computer Group (GCG), Madison, Wisc.), BLASTP, BLASTN, BLASTX (Altschul et al., J. Mol. Biol. 215, 403-410, 1990), DNASTAR (DNASTAR, Inc., Madison, Wisc.), and the FASTA program incorporating the Smith-Waterman algorithm (Pearson, W. R., Comput. Methods Genome Res., [Proc. Int. Symp., Meeting Date 1992, 111-120. eds: Suhai, Sandor. Publisher: Plenum, New York, N.Y., 1994). Within the context of this application it will be understood that where sequence analysis software is used for analysis, the results of the analysis will be based on the "default values" of the program referenced, unless otherwise specified. As used herein "default values" will mean any set of values or parameters which originally load with the software when first initialized.

Additional abbreviations used in this application are as follows: "hr" means hour(s), "min" means minute(s), "day" means day(s), "ml" means milliliters, "mg/ml" means milligram per milliliter, "L" means liters, "µl" means microliters, "mM" means millimolar, "µM" means micromolar, "pmol: means picomol(s), "° C." means degrees Centigrade or Celsius, "RT" means room temperature, "bp" means base pair, "bps" means base pairs, "kDa" means kilodaltons. "EtOH" means ethanol, "µg/L" means microgram per liter, "v/v/v", volume per volume per volume, "%" means per cent, "nM" means nano molar, "w/w" weight for weight, "ppm" means part per million.

Phylogenetic Typing

Methods for generating oligonucleotide probes and microarrays for performing phylogenetic analysis are known to those of ordinary skill in the art (Loy, A., et al., Appl. Environ. Microbiol., 70, 6998-700, 2004) and (Loy A., et al., Appl. Environ. Microbiol., 68, 5064-5081, 2002) and (Liebich, J., et al., Appl. Envrion. Microbiol., 72, 1688-1691, 2006). These methods are applied herein for the purpose of identifying microorganisms present in an environmental sample.

Specifically, conserved sequences of the 16S ribosomal RNA coding region of the genomic DNA, are used herein, however there are other useful methodologies for phylogenetic typing noted in the literature. These include: 23S rDNA or gyrase A genes and or any other highly conserved gene sequences. 16S rDNA is commonly used because the database of comparative known species is the largest to date.

The primers described herein were chosen as relevant to environmental samples from an oil reservoir (Grabowski, A., et al., FEMS Micro Eco, 544, 427-443, 2005) and by comparisons to other primer sets used for other environmental studies. A review of primers available for use herein can be found in Baker et al (G. C. Baker, G. C. et al., Review and re-analysis of domain-specific primers, J. Microbiol. Meth., 55, 541-555, 2003). Any primers which generate a part or whole of the 16S rDNA sequence would be suitable for the claimed method.

DNA extraction by phenol/chloroform technique is known in the art and utilized herein as appropriate for extracting DNA from oil contaminated environmental samples. However, there are other methodologies for DNA extraction in the literature that may be used in accordance with the present invention.

DNA sequencing methodologies that generate >700 bases of high quality sequence may be used for the type of plasmid based sequencing in accordance with the present invention in conjunction with a sequence quality analysis programs. The comparisons by homology using the BLAST algorithms to any comprehensive database of 16S rDNAs would achieve an acceptable result for identifying the genera of microorganisms present in the environmental sample. The most widely used databases are ARB (Ludwig, W., et al., ARB: a software environment for sequence data. Nucleic Acids Res. 32, 1363-1371, 2004) and NCBI.

Oil Well Sampling for Phylogenetic Studies

The samples used for this study were taken as described in Example 1. DNA was extracted from said samples followed by phylogenetic typing. Environmental samples for phylogenetic typing or mapping could come from any water associated with an oil reservoir system including water from plumbing and pipes at the production well, the water injection wells, cores taken directly from the geological formation with associated ground water or any other associated water source. Samples could be taken from any oil reservoir system. The samples described herein include environmental samples from heavy oil reservoirs on the North Slope of Alaska but could also include similar mesophillic heavy oil reservoirs in Russia or Canada or any thermophilic heavy oil reservoirs in South America, North Sea, Africa, Gulf Sea of any other location of any oil reservoir having any temperature or viscosity profile throughout the world.

Selection of Pure Cultures

Selection of pure cultures for use in this study was based on the genera discovered in the North Slope of Alaska reservoir production system. Genera identified from environmental samples were mapped by phylogenetics and used to select pure cultures for use in improving oil recovery. The pure culture species described herein were chosen for analysis based on phylogenetic mapping as related to the genera identified in the environmental samples. The analysis of said cultures resulted in identification of cultures with the ability to respire by denitrification and grow on oil without the addition complex carbon nutrients, as well as exhibiting one or more relevant functionalities for benefiting oil recovery.

The cultures identified and used herein are available from the American Type Culture Collection. There are many global public culture collections such as the German based DMS culture collection or the USDA NRRL collection and the National collection of Industrial Bacteria (NCIB) in England. Any publicly available culture collection would be usable for this kind of selection if it contains species in the correct genera.

Useful cultures for selection based on relatedness to environmental samples may also be selected for analysis of relevant functionalities based on literature references and association with petroleum or petroleum components.

Properties of Genera Observed in the Oil Reservoir System

The classical process of enrichment of environmental microbial isolates on a substrate of interest, i.e., crude oil, in anaerobic culture, requires extensive growth periods and multiple sequential transfers. By using the information gathered from the phylogenetic analysis of the target oil well described above, this laborious approach can be circumvented. Literature may be referenced to narrow selection of species from the genera identified as being part of the native population of the oil reservoir water system, or species may be chosen at random, or for their availability as a pure culture. Those microorganisms which are identifiable as pure cultures in the ATCC holdings or some other depository, can be procured and assayed for relevant functionalities, including ability to degrade crude oil under the conditions of interest.

In an aspect of the methods described herein, several known pure bacterial cultures were chosen based on their phylogenetic similarities to associated native microbial species. Consideration may also be given to known pure cultures identified as being isolated from a hydrocarbon environment or other relevant locations, or reportedly having some ability to affect hydrocarbons.

TABLE 1

LIST OF STRAINS OBTAINED FROM ATCC AND TESTED FOR GROWTH ON EITHER OIL OR OIL COMPONENTS

| Microorganism | ATCC# | Annotated metabolic capabilities |
| --- | --- | --- |
| Comamonas terrigena | 14635 | decomposes phenol and m-cresol |
| Fusibacter paucivorans | 700852 | thiosulfate-reducing from oil producing well, found in oil well production water sample |
| Marinobacterium georgiense | 33635 | found in oil well production water sample |
| Petrotoga miotherma | 51224 | from brine from petroleum reservoir, found in oil well production water sample |
| Shewanella putrefaciens | 51753 | from oil pipeline Alberta Canada, dehalogenates tetrachloromethane, found in oil well production water sample |
| Pseudomonas stutzeri | BAA-172 | strain OX1, degrades toluene/xylene aerobically, isolated from sludge |
| Vibrio alginolyticus | 14582 | Creosote tolerant |
| Thauera aromatica S100 Thauera aromatica T1 | 700265 | isolated from CA oil contaminated soil, degrades toluene, phenol toluene, phenol degradation |

Known pure cultures, once identified as belonging to genera relevant to an oil reservoir (as determined by phylogenetic typing) may be tested for relevant functionalities by conventional diagnostic assays, such as growth on selective media for denitrifyers, fermenters, sulfate reducers, methanogens, acetogenic and other physiological phenotypes.

In Example 5, ATCC strains that grow in or on crude oil under denitrifying anaerobic conditions were identified. As described in Example 5, all strains except *Clostridium amygdalium* grew under denitrifying conditions using oil as the sole carbon source. *Marinobacterium georgiense* had not previously been known to grow anaerobically under denitrifying conditions in the presence of oil. *Comamonas terrigena*, a soil bacterium, (originally filed as a Vibrio species) was a known facultative denitrifier but had not been reported to grow on oil components. While *Comamonas* species are known to degrade phenol under aerobic conditions, (Watanabe, et al., Appl. Environ. Microbiol., 64, 1203-1209, 1998) their ability to grow on oil under anaerobic conditions had not previously been reported. *Petrotoga miotherma*, a known thermophilic and strict anaerobic bacterium, was known to reduce sulfate and thiosulfate in the presence of oil at moderate to high temperatures (Davey, M. E., Syst. Appl. Microbiol., 16, 191-200, 1993) and, (Lien, T., et al., Int. J. Syst. Bacteriol., 48, 1007-1013, 1998). However, this organism was not known to use nitrate as an electron acceptor.

*Thauera aromatica* T1 grows on toluene and phenol under denitrifying conditions (Breinig, S. et al., J. Bacteriol., 182, 5849-5863, 2000) and (Leuthner, B., et al., J. Bacteriol., 182, 272-277, 2000) and *Thauera chlorobenzoica* degrades fluoro-, chloro-, and bromobenzoate under anaerobic, denitrifying conditions (Song, B. et al., Int. J. Syst. Evol. Microbiol., 51, 589-602, 2001). While simple aromatic components of oil can support growth of *Thauera* species, their growth in the presence of crude oil had not previously been documented. *Shewanella putrefaciens* anaerobically reduces oxidized metals such as iron and manganese. (Nealson, K. H., et al., Ann. Rev. Microbiol., 48, 311-343, 1994) and can also use a variety of reductants, including nitrate and nitrite (Nealson, K. H., et al., Appl. Eniron. Microbioil., 61, 1551-1554, 1995). While *Shewanella* had been reported to be associated with oil reservoir samples, it has not been previously demonstrated to grow on oil components directly. Some *Pseudomonas stutzeri* species, under aerobic conditions, degrade toluene, phenol, xylene, naphthalene and naphthalene related compounds (Bertoni, G. M., et al., Appl. Envrion. Microbiol., 64, 3626-3632, 1998). A particular strain of *P. stutzeri* anaerobically degrades naphthalene under denitrifying conditions (Rockne, K. J., Appl. Environ. Microbiol., 66, 1595-1601, 2000). Therefore, variants of *P. stutzeri* might have a higher likelihood of being able to grow on oil components. The lignin degrading microorganism, *Microbulbifer hydrolyticus*, had not been reported to be anaerobic, nor reduce nitrate.

Example 5 outlines details of growth of some of these strains on either various oil components or fractions. Since multiple strains could grow and accumulate biomass using some component of the crude oil as a source of carbon, these strains could be used to accumulate biomass in a reservoir in the presence of the appropriate electron acceptor and growth additives.

The following Examples therefore outline means to identify microorganisms that could be used to enhance oil recovery under economic conditions without the need for either nutrient supplementation, or selection by long term enrichment.

EXAMPLES

The present invention is further defined in the following Examples. It should be understood that these Examples, while indicating preferred embodiments of the invention, are given by way of illustration only. From the above discussion and the Examples outlined below, one skilled in the art can ascertain the essential characteristics of this invention, and without departing from the spirit and scope thereof, can make various changes and modifications of the invention to adapt it to various usages and conditions.

Collection of Environmental Samples

The oil/water samples were obtained from oil wells in Alaskan North Slope and 16S ribosomal DNA sequencing was used to identify the prokaryotic organisms present in this oil/water mixture. After examining the community analysis results of bacterial species in these samples, several additional similar species or species from the same genera, including those associated with other oil studies, from ATCC (Table 1) to include in the following Examples were chosen. These bacteria were then used in a screen for anaerobic growth in the presence of oil. Several species were shown to grow on oil as determined by quantitating nitrate depletion using ion chromatography (Table 3).

The ability to grow under denitrifying conditions using oil components as carbon substrates was unexpected for several of these species. For example, there have been no previous reports of the ability of a *Marinobacterium* to either reduce nitrate or grow anaerobically on crude oil. *Fusibacter* has not been reported to be capable of denitrification or of utilizing crude oil for growth.

Growth of Microorganisms

Techniques for growth and maintenance of anaerobic cultures are described in "Isolation of Biotechnological Organisms from Nature", (Labeda, D. P. ed. p 117-140, McGraw-Hill Publishers, 1990). Anaerobic growth is measured by nitrate depletion from the growth medium over time. Nitrate is utilized as the primary electron acceptor under the growth conditions used in this invention. The reduction of nitrate to nitrogen has been previously described (Moreno-Vivian, C., et al., J. Bacteriol.,181, 6573-6584, 1999). In some cases nitrate reduction processes lead to nitrite accumulation which is subsequently further reduced to nitrogen. Accumulation of nitrite is therefore also considered evidence for active growth and metabolism by microorganisms.

Gel Electrophoresis

Materials and methods suitable for gel electrophoresis may be found in "Current Protocols in Molecular Biology". Reagents were obtained, unless otherwise indicated, from either Invitrogen (Carlsbad, Calif.), Biorad (Hercules, Calif.) or Pierce Chemicals (Rockford, Ill.).

Ion Chromatography

To quantitate nitrate and nitrite ions in the aqueous media, an ICS2000 chromatography unit (Dionex, Banockburn, Ill.) was used. Ion exchange was accomplished on a AS15 anion exchange column using a gradient of potassium hydroxide. Standard curves were generated and used for calibrating nitrate, nitrite concentrations.

Example 1

Extraction of DNA from Reservoir Water Samples

Water samples were obtained from production well heads as mixed oil/water liquids in glass 1.0 L brown bottles, filled to the top, capped and sealed with tape to prevent gas leakage. Gas from inherent anaerobic processes sufficed to maintain anaerobic conditions during shipment. The bottles were shipped in large plastic coolers filled with ice blocks to the testing facilities within 48 hr of sampling.

After overnight settling and separation of the oil/water layers, 1-4 liters of water was removed from various bottles by pipetting and filtered through Whatman #1 (Brentford, Great Britain) glass fiber filters on a 47 mm glass chimney filter unit. The glass fiber filter collected residual oil, debris and >10 micron microbial cells. Subsequently, the water was filtered through sterile 0.22 micron Supor (Pall Corp., Ann Arbor, Mich.) nylon filters under vacuum. Microbial cells collected on the glass fiber filters or the Supor filters were resuspended in 4 ml of lysis buffer (100 mM Tris-HCL, 50 mM NaCl, 50 mM EDTA, pH 8.0) and mixed using a Vortex mixer for 60 sec. Reagents were added to a final concentration of 2.0 mg/ml lysozyme, 10 mg/ml sodium dodecyl sulfate, and 10 mg/ml sarkosyl to lyse the cells. After further mixing using a Vortex mixer, 0.1 mg/ml RNAse and 0.1 mg/ml Proteinase K were added to remove the RNA and protein contaminants. The mixture was incubated at 37° for 1.0 hr.

Post incubation, the filters were removed and an equivalent volume of Phenol:$CHCl_3$:isoamyl alcohol (25:24:1, v/v/v) was added to the tubes. The samples were extracted twice with Phenol:$CHCl_3$:isoamyl alcohol (25:24:1) and once with $CHCl_3$:isoamyl alcohol (24:1). To the aqueous layer, 1/10 volume of 5.0M NaCl and two volumes of 100% ethanol were added and mixed. The tubes were frozen at −20° C. for 16 hr and then centrifuged at 15,000×g for 30 min to pellet chromosomal DNA. The pellets were washed once with 70% ethanol, centrifuged at 15,000×g for 10 min, dried, resuspended in 100 µl of deionized water and stored at −20° C.

Example 2

Generation of rDNA PCR Fragments

To generate rDNA of PCR amplified fragments representative of microbial species in the pooled DNA samples, we chose primer sets from Grabowski et al. (supra). The combination of forward primer SEQ ID NO: 1 and SEQ ID NO: 2 was chosen to specifically amplify bacterial rDNA sequences.

The PCR amplification mix included: 1.0× GoTaq PCR buffer (Promega), 0.25 mM dNTPs, 25 pmol of each primer, in a 50 µl reaction volume. 0.5 µl of GoTaq polymerase (Promega) and 1.0 µl (20 ng) of sample DNA were added. PCR reaction thermocycling protocol was 5.0 min at 95° C. followed by 30 cycles of: 1.5 min at 95° C., 1.5 min at 53° C., 2.5 min at 72° C. and final extension for 8 min at 72° C. in a Perkin Elmer 9600 thermocycler (Waltham, Mass.). This protocol was also used with cells from either purified colonies or mixed species from enrichment cultures.

The 1400 base pair amplification products were visualized on 1.0% agarose gels. The PCR reaction mix was used directly for cloning into pPCR-Topo4 vector using the TOPO TA cloning system (Invitrogen) using the manufacturer's recommended protocol. DNA was transformed into TOP10 chemically competent cells selecting for ampicillin resistance. Individual colonies were picked and grown in microtiter plates for sequence analysis.

Example 3

Plasmid Template Preparation

Large-scale automated template purification systems used Solid Phase Reversible Immobilization (Agencourt, Beverly, Mass.) (DeAngelis, M. M., et al., Nucleic Acid Res., 23, 4742-4743, 1995) The SPRI® technology uses carboxylate-coated, iron-core, paramagnetic particles to capture DNA of a desired fragment length based on tuned buffering conditions. Once the desired DNA is captured on the particles, they can be magnetically concentrated and separated so that contaminants can be washed away.

The plasmid templates were purified using a streamlined SprintPrep™ SPRI protocol (Agencourt).This procedure harvests plasmid DNA directly from lysed bacterial cultures by trapping both plasmid and genomic DNA to the functionalized bead particles and selectively eluting only the plasmid DNA. Briefly, the purification procedure involves addition of alkaline lysis buffer (containing RNase A) to the bacterial culture, addition of alcohol based precipitation reagent including paramagnetic particles, separation of the magnetic particles using custom ring based magnetic separator plates, 5× washing of beads with 70% ETOH and elution of the plasmid DNA with water.

Example 4

RDNA Sequencing, Clones Assembly and Phylogenetic Analysis

DNA Sequencing

DNA templates were sequenced in a 384-well format using BigDye® Version 3.1 reactions on ABI3730 instruments (Applied Biosystems, Foster City, Calif.). Thermal cycling was performed using a 384-well thermocycler. Sequencing reactions were purified using Agencourt's CleanSeq® dye-terminator removal kit (Agencourt) as recommended by the manufacturer. The reactions were analyzed using a model ABI3730XL capillary sequencer using an extended run module developed at Agencourt. All reads were processed using Phred base calling software (Ewing et al., Genome Res., 8, 175-185, 1985) and constantly monitored against quality metrics.

Assembly of rDNA Clones

A file for each rDNA clone was generated. The assembly of the sequence data generated for the rDNA clones was performed by the PHRAP assembly program (Ewing, et al., Genome Research 8, 175-185, 1985). Proprietary scripts generate consensus sequence and consensus quality files for > one overlapping sequence read.

Analysis of rDNA Sequences

Each assembled sequence was compared to the NCBI (rDNA database; ~260,000 rDNA sequences) using the BLAST algorithm program (Altschul, supra). The BLAST hits were used to group the sequences into homology clusters with at least 98% identity to the same NCBI rDNA fragment. The homology clusters were used to calculate proportions of particular species in any sample. Because amplification and cloning protocols were identical for analysis of each sample, the proportions could be compared from sample to sample. This allowed comparisons of population differences in samples taken at different times, locations, enrichment selections or isolated colonies.

Ribosomal DNA (Small Subunit rDNA) Phylogenetic Analyses

A representative sequence of each homology cluster was chosen to generate the phylogenetic tree relationships. Small Subunit (SSU) rDNA sequences were aligned to their nearest taxonomic affiliates within the SILVA reference database (release 90, http://silva.mpi-bremen.de/) using the ARB_EDIT4 tool in the ARB program (Ludwig, W. et al., Nucleic Acid Res., 32, 1363-1371, 2004); taxonomic assignments were verified by submitting sequences to the Sequence Match tool at the Ribosomal Database Project (RDP) II (Cole, J. R., et al., Nucleic acid Res., 33, D294-D296, 2005).

TABLE 2

LIST OF GENERA FOUND IN THE ALASKAN OIL RESERVOIR PRODUCTION WATER. ITALICIZED GENERA MATCH CULTURE ISOLATES FROM ATCC USED IN THIS STUDY
Genera identified in the Alaska oil reservoir system using rDNA sequence comparisons

| Unclassified and Thermotogae |
|---|
| Chloroflexi |
| Petratoga/thermotogae |
| Proteobacteria, gamma |
| |
| *Shewanella* |
| *Vibrio* |
| *Marinobacterium* |
| *Pseudomonas* |
| Proteobacteria, epsilon |
| |
| Arcobacter |
| *Agrobacterium* |
| Proteobacteria, delta |
| |
| Desulfolobus |
| Flexistipes/Deferribacter, delong |

TABLE 2-continued

LIST OF GENERA FOUND IN THE ALASKAN OIL
RESERVOIR PRODUCTION WATER. ITALICIZED GENERA
MATCH CULTURE ISOLATES FROM ATCC USED IN THIS STUDY
Genera identified in the Alaska oil reservoir system using
rDNA sequence comparisons Desulfocaldus
Desulfomicrobium
Actinobacter
Pelobacter
Bacteroides, unclassified, spirochaetes Bacteroides
WS6 group
Spirochaeta
*Firmicutes*

Acetobacterium
Alkalibacter
*Fusibacter*
*Fusibacter paucivorans*
Desulfobacterium
*Clostridium*

Example 5

Screening of the ATCC Bacterial Strains for Growth on Oil of Oil Components

The freeze dried samples obtained from ATCC were revived and grown according to their recommended procedures, and aliquots were used as inocula for experimental and control growth studies. A minimal salts medium usually used for growth of denitrifying bacteria (Table 3) was used to grow various organisms tested in this Example. The carbon and energy source for growth was provided by either autoclaved crude oil or a mixture of 0.25% yeast extract and 0.2% succinate which was used as the positive control. Sodium nitrate ($NO_3^-$ ~1200 ppm) was added as the primary electron receptor. The medium was deoxygenated by sparging the filled vials with a mixture of nitrogen and carbon dioxide followed by autoclaving. All manipulations of bacteria were done in an anaerobic chamber (Coy Laboratories Products, Inc. Grass Lake, Mich.). Anaerobic growth at 25° C. was monitored by both observing visual turbidity in the vials and nitrate reduction for two weeks. Ion chromatography was used to measure nitrate and nitrite levels weekly.

TABLE 3

MINIMAL SALTS MEDIUM

| Growth component | Final concentration | Chemical source |
|---|---|---|
| Nitrogen | 18.7 μM | $NH_4Cl$ |
| Phosphorus | 3.7 μM | $KH_2PO_4$ |
| Magnesium | 984 μM | $MgCl_2 \cdot 6H_2O$ |
| Calcium | 680 μM | $CaCL_2 \cdot 2H_2O$ |
| Sodium chloride/ | 172 mM | NaCl |
| Sodium iodide | 1% | NaI |
| Trace metals | | |
| | 670 μM | nitrilotriacetic acid |
| | 15.1 μM | $FeCl_2 \cdot 4H_2O$ |
| | 1.2 μM | $CuCl_2 \cdot 2H_2O$ |
| | 5.1 μM | $MnCL_2 \cdot 4H_2O$ |
| | 12.6 μM | $CoCl_2 \cdot 6H_2O$ |
| | 7.3 μM | $ZnCl_2$ |

TABLE 3-continued

MINIMAL SALTS MEDIUM

| Growth component | Final concentration | Chemical source |
|---|---|---|
| | 1.6 μM | $H_3BO_3$ |
| | 0.4 μM | $Na_2MoO_4 \cdot 2H_2O$ |
| | 7.6 μM | $NiCl_2 \cdot 6H_2O$ |
| pH buffer (7.5 final) | 10 mM | Hepes |
| Selenium-Tungstate | 22.8 nM | $Na_2SeO_3 \cdot 5H_2O$ |
| | 24.3 nM | $Na_2WO_4 \cdot 2H_2O$ |
| Bicarbonate | 23.8 nM | $NaHCO_3$ |
| vitamins | 100 μg/L | vitamin B12 |
| | 80 μg/L | p-aminobenzoic acid |
| | 20 μg/L | nicotinic acid |
| | 100 μg/L | calcium pantothenate |
| | 300 μg/L | pyridoxine hydrochloride |
| | 200 μg/L | thiamine-$HCl \cdot 2H_2O$ |
| | 50 μg/L | alpha-lipoic acid |
| Electron acceptor | 0.4 g/L | $NaNO_3$ |

The pH of the medium was adjusted to 7.5.

Several of the bacteria listed in Table 1 utilized components of crude oil, under denitrifying conditions, as the sole carbon source for growth. Growth was determined by turbidity visualization and nitrate reduction and results are shown in Table 4. Turbidity was observed and samples taken starting at 7 days post inoculation. Cultures which were turbid at day 7 were given a relative growth rate of 1 (fastest). Fractional values indicate proportionately longer times until turbidity was observed. Relative growth rate based on nitrate levels was defined by setting a relative growth rate number of 1 to those cultures which reduced the entire 250 ppm of available nitrate by Day 7. Fractional values indicate proportionately longer times to complete nitrate reduction.

TABLE 4

RELATIVE GROWTH RATE WAS DEFINED AS 1/DAYS
UNTIL OBSERVABLE TURBIDITY AND RELATIVE RATE
OF TOTAL NITRATE DEPLETION WHEN OIL WAS THE
SOLE CARBON SOURCE. A VALUE OF 1 INDICATES
TURBIDITY OR COMPLETE NITRATE REDUCTION
AT DAY 7

| Microorganisms | relative growth rate by turbidity | relative growth rate by nitrate reduction |
|---|---|---|
| *Clostridium amygdalinum* | 0 | 0 |
| *Comamonas terrigena* | 1 | 0.5 |
| *Marinobacterium georgiense* | 0.25 | 1.0 |
| *Microbulbifer hydrolyticus* | 1 | 0.5 |
| *Petrotoga miotherma* | 0.125 | 0.5 |
| *Shewanella putrefaciens* | 1 | 0.5 |
| *Thauera aromatica* T1 | 0.25 | 1.0 |
| *Thauera aromatica* S100 | 0.25 | 0.5 |
| *Thauera chlorobenzoica* | 1 | 1 |
| *Pseudomonas stutzeri* | 1 | 0.3 |

*Marinobacterium georgiense* (ATCC#33635), *Thauera aromatica* T1 (ATCC#700265), and *Thauera chlorobenzoica* (ATCC#700723) all had reduced nitrate by day 7. Additionally, *Petrotoga miotherma* (ATCC#51224), *Shewanella putrefaciens* (ATCC#51753), *Thauera aromatica* S100 (ATCC#700265), *Comamonas terrigena* (ATCC#14635), and *Microbulbifer hydrolyticus* (ATCC#700072), had used all available nitrate by day 14. Several of the species had also accumulated nitrite by day 7, including *Marinobacterium georgiense*, *Thauera aromatica* T1, *Thauera chlorobenzoica*, *Shewanella putrefaciens*, and *Thauera aromatica* S100. By day 14 *Microbulbifer hydrolyticus* and *Comamonas terrigena* also accumulated nitrite. *Clostridium amygdalinum* (#BAA501) did not grow on oil, but did grow with yeast extract and succinate.

The majority of the strains identified using this process grew on crude oil under denitrifying conditions.

Example 6

Discovery of Oil Components Utilized as Carbon Substrates by Isolated Species

Some of the ATCC strains described in Table 1 were grown in the presence of various oil component model substrates under denitrifying conditions. The following substrates were examined: Decane, representative of long chain hydrocarbons; Toluene, representative of simple aromatic hydrocarbons; Naphthalene representing polyaromatic hydrocarbons, an "aromatics" fraction which was a mixture of higher molecular weight polyaromatic hydrocarbons derived by distilling the crude oil using ASTM D2892 and collecting the undistilled fraction from this procedure and using ASTM D4124-01 on this undistilled fraction to produce a heavy aromatic fraction (Manual on Hydrocarbon Analysis: 6th Edition", A. W. Drews, editor, Printed by ASTM, West Conshohocken, Pa., 19428-2959, 1998.). The "aromatics" fraction contained 0.23% toluene as an additive for resuspension.

As in Example 5, cultures were monitored for growth (turbidity) and nitrate reduction (nitrate and nitrite concentrations). In order to observe changes in oil composition after long term exposure to growing bacterial cultures, the growth medium was supplemented with additional nitrate as the initial nitrate was depleted.

Bacteria for inoculation of the test system were grown as recommended by ATCC in the medium optimized for the particular species. The species included in this study were: *Marinobacterium georgiense*, *Thauera aromatica* T1, *Thauera chlorobenzoica*, *Petrotoga miotherma*, *Shewanella putrefaciens*, *Thauera aromatica* S100, *Comamonas terrigena*, and *Microbulbifer hydrolyticus* (Table 1). Cultures (4.0 ml) were centrifuged (10,000×g, 5-7 min, room temperature), under anaerobic conditions, in a microcentrifuge and the pellets were resuspended in 4.0 ml of the minimal salts medium (Table 3) using a syringe and an 18 gauge needle. The cells were washed twice using this process before they were resuspended in 3.0 ml of the medium and 0.5 ml of this suspension was used to inoculate each experimental vial.

All media, culture, and sampling protocols were as in Example 5. Sodium nitrate was added to the minimal salts medium at a concentration of 0.4 g/L which translates to 250 ppm of nitrate. A positive growth control consisting of 0.25% yeast extract and 0.2% succinate was included in the test. Decane and toluene were filter sterilized (0.2 micron, Supor filters) and degassed with nitrogen/carbon dioxide mixed gas. Naphthalene was dissolved in toluene at 500 mg/L, filter sterilized, and 15 µl of this solution added to sterile vials. Vials were dried overnight to evaporate the toluene and placed in the anaerobic chamber to equilibrate for several hours before culture was added. The "aromatic" fraction of oil (prepared using ASTM D4124-01 on the undistilled fraction from procedure ASTM D2892, supra) and whole crude oil were degassed then autoclaved. Under anaerobic conditions, 15 ml aliquots of the medium were combined with washed, resuspended cells in sterile 20 ml serum vials. Additionally either 0.25% yeast extract and 0.2% succinate 0.1% decane, 0.03% toluene, or 0.0050% naphthalene was added. For the complex hydrocarbons, 10 ml of medium plus cells was added to vials and either 5.0 ml of 10% "aromatics" fraction (w/w) in hexamethylnonane, as an inert organic phase or 5.0 ml of crude oil was added.

Turbidity was monitored visually. Nitrate and nitrite levels were determined by ion chromatography as described above. Sodium nitrate (350 ppm final conc.), was added when initial nitrate was depleted for up to 50 days. Several microorganisms reduced nitrate while growing on either the model substrates, the "aromatic" fraction or the crude oil. In cultures of some of microorganisms that utilized nitrate, some nitrite accumulated, however, the majority of the nitrogen probably was reduced to nitrogen ($N_2$).

Figure 1:
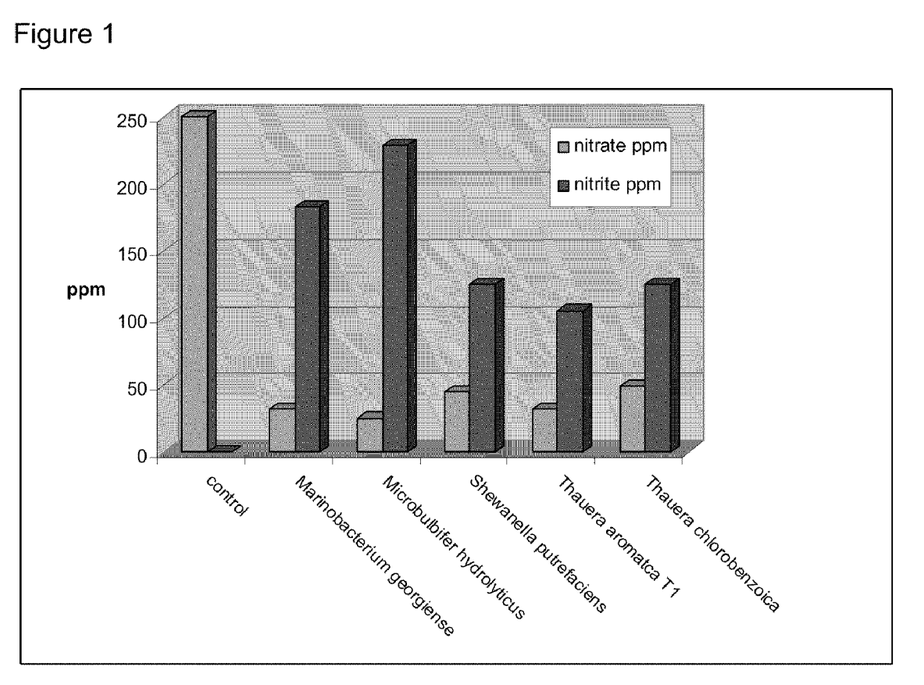
FIG. 1—Depicts nitrate and nitrite concentrations (ppm) after 36 days of growth on crude oil. Nitrate and nitrite were measured using ion exchange chromatography.

Growth was correlated to depletion of nitrate and accumulation of nitrite. Only *Shewanella* and *T. aromatica* S100 showed limited growth on decane as determined by minimal reduction of nitrate. *Marinobacterium, Shewanella, Thauera* S100, *Thauera aromatica*, *T. chlorobenzoica*, and *Petrotoga* had limited growth on toluene. Naphthalene supported some growth of *T. aromatica* S100. Growth of *Marinobacterium* and *Thauera* T1 on the "aromatic" fraction of the oil was accompanied by complete nitrogen depletion. *Shewanella* and *T. chlorobenzoica* also depleted nitrate when grown on the crude oil but had limited growth on the "aromatics" fraction. FIG. 1 shows nitrate/nitrite measurements after 36 days of growth on crude oil. *Microbulbifer* and *Marinobacterium* had steady depletion of nitrate on oil with a concurrent accumulation of nitrite. Nitrite accumulated by 36 days but was further reduced by 50 days by *Shewanella, T. aromatica* T1 and *T. chlorobenzoica*.

Example 7

Screening of Bacterial Isolates for Enhanced Oil Release

Micro sand Column Oil Release Test

Isolated bacterial strains were examined using a micro sand column assay to visualize oil release. A micro sand column consisted of an inverted glass Pasteur pipet containing sea sand (EMD chemicals, La Jolla, Calif.) which had been coated with crude oil and allowed to age for at least one week. Specifically, 280 ml of sterile sand and 84 ml of sterilized oil (same oil used in Examples 2 though 5) were combined in an anaerobic environment. The mixture was stirred for 5 min twice each day and allowed to age for six days under nitrogen. The barrels of glass Pasteur pipets were cut to half height and autoclaved. The cut end of the pipet was plunged into the sand/oil mix and the core filled to about 1.0 inch. The cut end of the pipet containing the oil/sand mixture was then placed into a glass test tube containing microbial cultures. The apparatus was sealed inside glass vials in an anaerobic environment and the oil release from the sand observed in the tapered end of each pipet (FIG. 2). Oil released from the sand collects in the narrow neck of the Pasteur pipets or as droplets on the surface of the sand layer. Cultures which enhanced release of oil over background (sterile medium) were presumed to have altered the interaction of the oil with the sand surface and could potentially act to enhance oil recovery in a petroleum reservoir.

In this Example, inoculum was grown to turbidity using either the minimal salts medium shown in Table 2 with 0.4% succinate as carbon source or in Luria Broth. The concentration of each species, listed in Table 4 below, was normalized to $OD_{600}$ of 1.0 or diluted 1:10 for a final $OD_{600}$ of 0.1. All operations for preparation of the micro sand columns, inoculation and growth were done using sterile techniques in an anaerobic glove bag. Inocula (4 ml) from either the $OD_{600}$ of 1.0 or $OD_{600}$ of 0.1 were added to small glass tubes and the micro sand columns immersed in the medium/cell mixtures with the narrow neck of the Pasteur pipets pointing up. The outer vials were sealed in the anaerobic chamber and allowed to incubate at ambient temperatures for 24 hr. Table 5 shows the strains tested and the observations of oil release after 24 hr.

$OD_{600}$=1, the highest level of oil release was observed with *Fusibacter paucivorans* while *Thauera aromatics* showed the highest oil release at cell concentrations of $OD_{600}$=0.1. Although *Marinobacterium georgiense*, has the ability to grow well on oil as the sole carbon source, it did not release oil under these experimental conditions. This observation could be rationalized by sensitivity of oil release by this strain to factors such as the growth stage and/or specific medium requirements. These experiments demonstrated that strains selected via phylogenetic analyses can be effective in growth on oil under anaerobic denitrifying conditions and in oil release in the sand/oil release test described here.

SEQUENCE LISTING

<160> NUMBER OF SEQ ID NOS: 2

<210> SEQ ID NO 1
<211> LENGTH: 20
<212> TYPE: DNA
<213> ORGANISM: artificial sequence
<220> FEATURE:
<223> OTHER INFORMATION: Primer

<400> SEQUENCE: 1
agagtttgat ymtggctcag               20

<210> SEQ ID NO 2
<211> LENGTH: 17
<212> TYPE: DNA
<213> ORGANISM: artificial sequence
<220> FEATURE:
<223> OTHER INFORMATION: Primer

<400> SEQUENCE: 2
gacgggggtg wgtrcaa                  17

TABLE 5

RELEASE OF OIL FROM MICROSAND COLUMNS BY ISOLATED BACTERIAL STRAINS

| Bacterial isolate | inoculum $OD_{600}$ = 1 | inoculum $OD_{600}$ = 0.1 |
|---|---|---|
| *Petrotoga miotherma* | some release | no release |
| *Marinobacterium georgiense* | no release | no release |
| *Fusibacter paucivorans* | oil release | no release |
| *Thauera aromatica* T1 | some release | oil release |

Of the selected isolates screened in this Example, 3 different genera demonstrated various levels of oil release. At

The invention claimed is:

1. A method for identifying microorganisms from an oil reservoir useful for oil recovery comprising:
   (a) providing an environmental sample from an oil reservoir comprising an indigenous microbial population;
   (b) identifying the microbial genera present in said environmental sample by phylogenetic typing;
   (c) selecting one or more known pure culture species from a non-oil reservoir source corresponding to the genera identified in (b); and
   (d) screening the pure culture species identified in (c) for relevant functionalities to identify those microbial genera useful for enhanced oil recovery, wherein the relevant functionalities are selected from the group consisting of: the ability to use at least one component available in the oil reservoir as a carbon source; the ability to use at least one component in injected or produced water from the oil reservoir; the capability of achieving a desired growth rate in the presence of oil; and the ability to grow optimally in an oil well environment; and combinations thereof.

2. The method of claim 1, wherein phylogenetic typing is based on the identification of 16S rDNA sequences.

3. The method of claim 2 where the 16S rDNA sequences are identified using molecular probes selected from the group consisting of SEQ ID NO: 1 and SEQ ID NO: 2.

4. The method of claim 1, wherein the microbial genera identified in step (b) are selected from the group consisting of: *Chloroflexi, Petratoga, Arcobacter, Argrobacterium, Acetobacterium, Shewanella, Spurochaeta, Alkalibacter, Actinobacter, Pelobacter, Clostridium, Deslfomicrobium, Vibrio, Marinobacterium, Pseudomonas*, and *Fusibacterium*.

5. The method of claim 1, wherein the known pure culture species of step (c) are selected from the group consisting of *Fusibacter, Marinobacter, Petrotoga, Shewanella, Pseudomonas, Thauera Comamonas* and *Vibrio*.

6. A method for enhancing oil recovery from an oil well comprising:
(a) providing an environmental sample from an oil reservoir comprising an indigenous microbial population;
(b) identifying the microbial genera present in said environmental sample by phylogenetic typing;
(c) selecting one or more known pure culture species from a non-oil reservoir source corresponding to the genera identified in (b);
(d) screening the pure culture species identified in (c) for relevant functionalities to identify those microbial genera useful for enhanced oil recovery, wherein the relevant functionalities are selected from the group consisting of: the ability to use at least one component available in the oil reservoir as a carbon source; the ability to use at least one component in injected or produced water from the oil reservoir; the capability of achieving a desired growth rate in the presence of oil; and the ability to grow optimally in an oil well environment; and combinations thereof; and
(e) inoculating into an oil well at least one culture of the microbial genera identified in (d) under conditions whereby oil recovery is enhanced.

7. The method of claim 6 wherein the relevant functionalities provide for enhanced oil recovery by altering permeability of the subterranean formation to improve water sweep efficiency, production of biosurfactants to decrease surface and interfacial tensions, change wettability, produce polymers which facilitate mobility of petroleum, produce low molecular weight acids which cause rock dissolution, and generate gases (predominantly $CO_2$) to increase formation pressure and reduce oil viscosity to ease recovery and processing of heavy crude oil.

8. The method of claim 6, wherein the enhanced oil recovery occurs by a reduction in crude oil viscosity by growth of a species in (d), wherein said growth results in the production of any one of biosurfactants, carbon dioxide, or cell mass, selective degradation of high molecular weight components in the oil well or combinations thereof.

9. The method of claim 6 wherein said enhanced oil recovery occurs by growth of a species of (d) in an oil well under anaerobic and denitrifying conditions substantially without corrosion of recovery and processing hardware.

10. The method of claim 6, further comprising the step of modifying the oil well environment by adding simple nitrites or simple nitrates to the oil well to promote growth of microbes in the oil well to enhance oil recovery without additional carbon sources.

11. The method of claim 6, comprising modifying the oil well reservoir to enhance the growth of at least one microbial genus identified in step (b), where said genus outcompetes the members of all other genera in the oil reservoir.

12. The method of claim 6, wherein said oil well environment favors microbes selected from the group consisting of mesophiles, thermophiles, halophiles, acidophiles, alkaliphiles, psychrophiles, and piezophiles.

13. A method according to claim 6 wherein at step (e) the oil well is amended with nitrate.

\* \* \* \* \*